(12) United States Patent
Storz

(10) Patent No.: US 7,846,178 B2
(45) Date of Patent: Dec. 7, 2010

(54) MEDICAL CUTTING AND/OR HOLDING INSTRUMENT

(75) Inventor: Martin Storz, Tuttlingen (DE)

(73) Assignee: Karl Storz GmbH & Co. KG (DE)

( * ) Notice: Subject to any disclaimer, the term of this patent is extended or adjusted under 35 U.S.C. 154(b) by 410 days.

(21) Appl. No.: 11/678,955

(22) Filed: Feb. 26, 2007

(65) Prior Publication Data

US 2007/0198056 A1    Aug. 23, 2007

Related U.S. Application Data

(63) Continuation of application No. PCT/EP2005/009130, filed on Aug. 24, 2005.

(30) Foreign Application Priority Data

Aug. 25, 2004    (DE) ................ 10 2004 041 080

(51) Int. Cl.
*A61B 17/00* (2006.01)
*A61B 18/18* (2006.01)

(52) U.S. Cl. .................. 606/205; 606/50; 606/51; 606/52

(58) Field of Classification Search ........ 606/205, 606/210

See application file for complete search history.

(56) References Cited

U.S. PATENT DOCUMENTS 1,521,689 A * 1/1925 King .................. 294/99.2
2001/0051805 A1 * 12/2001 Hirano et al. ........... 606/52
2002/0128649 A1 * 9/2002 Bacher et al. ........... 606/46
2004/0153061 A1 * 8/2004 Wang .................. 606/51

FOREIGN PATENT DOCUMENTS

| DE | 20 2004 000 276 U1 | 7/2004 |
| WO | WO 2005/079680 A2 | 9/2005 |

OTHER PUBLICATIONS

International Search Report, Dec. 21, 2005, 2 pages.

* cited by examiner

*Primary Examiner*—Eduardo C Robert
*Assistant Examiner*—Kevin Everage
(74) *Attorney, Agent, or Firm*—St. Onge Steward Johnston & Reens LLC

(57) ABSTRACT

The invention relates to a medical cutting and/or holding instrument having a shaft, a tool mounted on the distal end of the shaft and consisting of two jaw members, and also having a handle that is mounted on the proximal end of the shaft, consists of two gripping members, and serves to open and close the jaw members of the tool. In order to produce a simply constructed and easily cleanable medical cutting and/or holding instrument, it is proposed according to the invention that the shaft should consist of two shaft rods, each configured without joints as a single construction with one gripping member of the handle.

13 Claims, 4 Drawing Sheets

MEDICAL CUTTING AND/OR HOLDING INSTRUMENT

CROSS-REFERENCE TO RELATED APPLICATIONS

The present application is a continuation of pending International patent application PCT/EP2005/009130 filed on Aug. 24, 2005 which designates the United States and claims priority from German patent application 10 2004 041 080.1 filed on Aug. 25, 2004, the content of which is incorporated herein by reference.

FIELD OF THE INVENTION

The invention relates to a medical cutting and/or holding instrument having a shaft, a tool mounted on the distal end of the shaft and consisting of two jaw members, and also having a handle that is mounted on the proximal end of the shaft, consists of two gripping members, and serves to open and close the jaw members of the tool.

BACKGROUND OF THE INVENTION

Medical cutting and/or holding instruments configured as shaft instruments are known in the prior art in a vast range of embodiments. Shaft instruments known in the prior art, both on the jaw side, that is, on the distal end, and on the handle side or proximally, include jointed constructions that make it possible, by actuating a rotatable gripping member of the handle, to rotate the jaw members of the tool with respect to one another for opening and closing. The jaw members in this case are actuated by the rotatable gripping member, as a rule, by means of a push/pull rod that is mounted so that it can slide in the hollow instrument shaft.

The disadvantage with these known medical cutting and/or holding instruments that are configured as shaft instruments is that both their jaw mechanism and the mechanism of the gripping members of the handle that can rotate with respect to one another require joint constructions that use expensive production technology. In addition to this high cost of components and assembly, with hollow-shaft instruments known in the art it is extremely essential that they are configured so they can be disassembled in order to ensure impeccable cleaning of the instrument.

It is consequently the object of the invention to design a medical cutting and/or holding instrument of the aforementioned type in such a way that it can be constructed simply and is easy to clean.

SUMMARY OF THE INVENTION

This object is fulfilled according to the invention in that the shaft consists of two shaft rods, each configured without joints as a single piece with one gripping member of the handle.

As a result of the jointless single-unit construction of the shaft rod and gripping member of the handle, it is possible to dispense entirely with a joint mechanism in the area of the handle. In addition, the number of individual components is clearly reduced in comparison with hollow-shaft instruments known in the prior art, so that a simpler and more cost-effective installation is possible.

According to a first practical embodiment of the invention, it is proposed that the gripping members of the handle should be connected to one another by means of a coupling element. By means of this coupling element the gripping members of the handle are joined together to form a single unit, so that the handling of the instrument can be simplified.

To reduce still further the number of individual components, it is proposed according to a preferred embodiment of the invention that the handle that includes the two gripping members should be configured as a single-piece unit. In this construction, at least the two shaft rods and the two gripping members of the handle constitute only a single component. Such a surrounding framework construction produced preferably from prefabricated rod material can be manufactured simply and at reasonable cost, and in addition can be cleaned reliably without disassembly.

The jaw members of the tool are actuated by means of the gripping members of the handle in such a way that the gripping members of the handle can be displaced with respect to one another by spring elasticity. The spring elasticity of the gripping members, which are preferably made of precious metal, replace the costly joint mechanism of the known gripping constructions in the construction according to the invention.

To facilitate the gripping of the handle for the operator and to ensure a secure, precise operation of a medical cutting and/or holding instrument according to the invention, according to a first embodiment of the invention the handle is configured as flattened, at least in the area of one gripping member.

Alternatively, it is proposed with the invention that on at least one gripping member of the handle, at least one finger groove is configured, or on at least one gripping member of the handle a gripping plate is produced in order to allow stationary gripping of the handle.

It is further proposed with the invention that one jaw member of the tool is of single unit construction and configured as a rigid single piece with a shaft rod, and the other jaw member is mounted so that it can rotate around coupling points on the other shaft rod as well as on the rigid jaw member. As a result of the single-unit rigid configuration of the one jaw member, the number of individual parts is further reduced. Preferably, the jaw construction according to the invention is configured in such a way that various transmission ratios can be achieved. For this purpose it is proposed that the distance of the support points of the rotatable jaw member can be modified.

In particular for the configuration of the medical instrument according to the invention as a holding instrument, the gripping members of the handle and/or the shaft rods, at least with the tool in closed position, can be fixed in their particular position with respect to one another by means of a stopping mechanism Besides the use of the medical instruments according to the invention as mere cutting and/or holding instruments, these instruments can also be configured in such a way that they can be used as a monopolar or bipolar instrument for electro-surgery. In so-called electro-surgery, high-frequency power is directed to the surgical area by the medical instrument and transformed in the tissue into heat energy, while temperatures of about 60 to 100 degrees C. develop. This electro-surgery is used to coagulate tissue and small vessels as well as to cut or sever tissue.

For using an inventive medical instrument in electro-surgery, it is proposed that the gripping members of the handle should be connected with a connecting plug by which the high-frequency current is introduced into the instrument and, in bipolar application, is also directed out of it again.

In the configuration of the handle with two separate gripping members, it is proposed with the invention that the connecting plug should be configured as a coupling element that connects the two gripping members of the handle with one another.

The shaft rods running separately from one another, with the gripping members configured onto them without joints as a single unit, offer decidedly favorable insulating conditions when used to convey electric high-frequency current inward and outward. For this purpose, according to a practical embodiment of the invention, it is proposed that all current-conducting parts, including the two jaw members of the tool, should be configured as electrically insulated, in particular by means of a contracting hose.

To prevent premature transmission of current into the current-draining shaft rod, it is proposed with the invention, finally, that the rotatable jaw member should be mounted on the rigid jaw member and on the shaft rod by means of an electrically isolated jointed strip.

Additional characteristics and advantages of the invention can be seen with reference to the related illustrations, in which six embodiments of a medical cutting and/or holding instrument according to the invention are presented by way of example.

BRIEF DESCRIPTION OF THE DRAWINGS

FIG. 4b shows a rear view of the instrument shown in FIG. 4a.

FIG. 4c shows an enlarged detail view of the detail Ivc shown in FIG. 4a.

FIG. 6b shows an enlarged and partly cut-out detailed side view of the instrument shown in FIG. 6a.

DETAILED DESCRIPTION OF THE INVENTION

Figure 1:
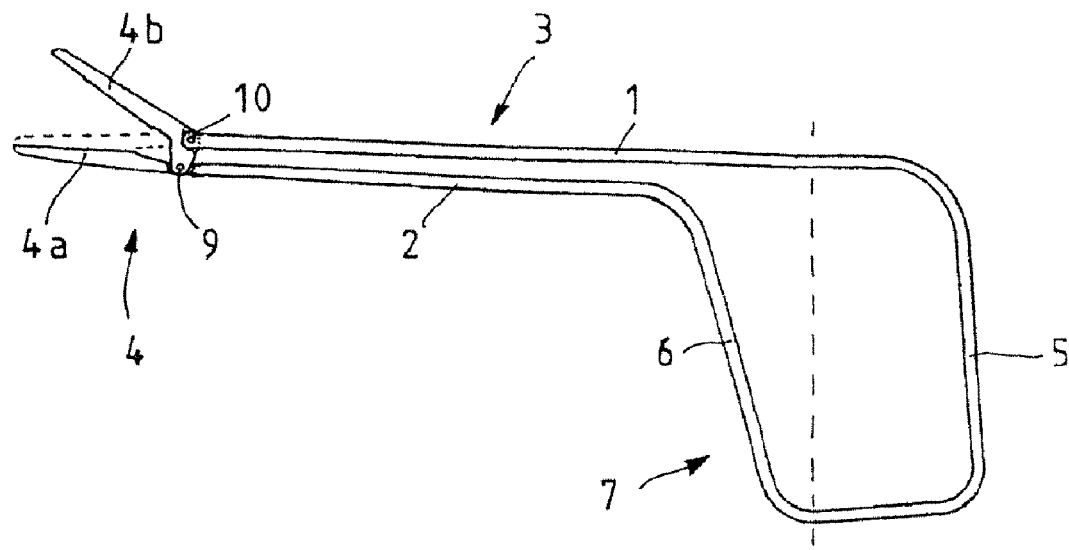
FIG. 1 shows a side view of a first embodiment of a medical cutting and/or holding instrument according to the invention.

The medical cutting and/or holding instruments shown in side view in FIGS. 1, 2, 3, 4a, 5, and 6a consist essentially of a shaft 3 consisting of two separate shaft rods 1 and 2, a tool 4 positioned on the distal end of the shaft 3 and consisting of two jaw members 4a and 4b, as well as a handle 7 positioned on the proximal end of the shaft 3 and consisting of two gripping members 5 and 6.

The medical cutting and/or holding instruments shown in the illustrations have the particularity that every gripping members 5 and 6 of the handle 7 and the particular related shaft rods 1 and 2 of the shaft 3 are configured as single unit constructions without joints.

Figure 2:
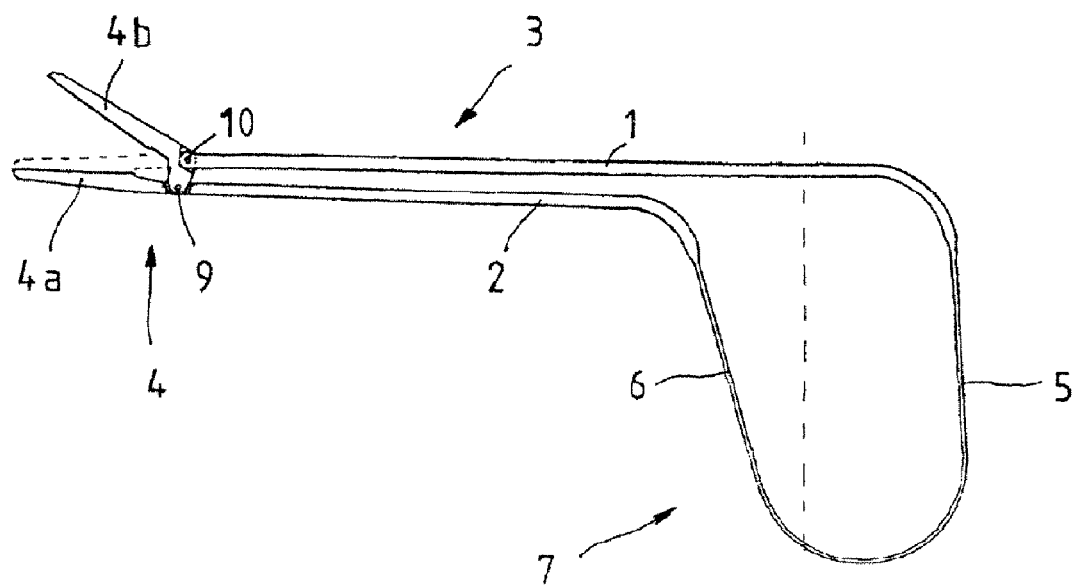
FIG. 2 shows a side view of a second embodiment of a medical cutting and/or holding instrument according to the invention.
Figure 3:
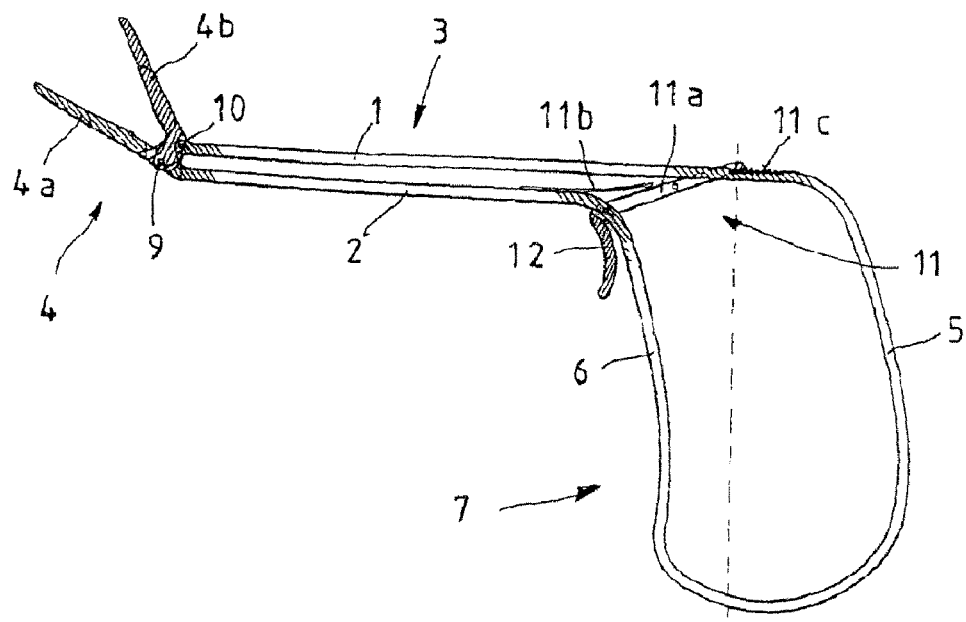
FIG. 3 shows a side view of a third embodiment of a medical cutting and/or holding instrument according to the invention.
Figure 4A:
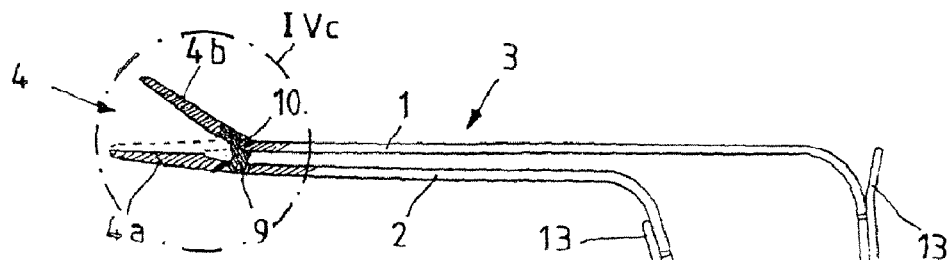
FIG. 4a shows a side view of a fourth embodiment of a medical cutting and/or holding instrument according to the invention.
Figure 4B:
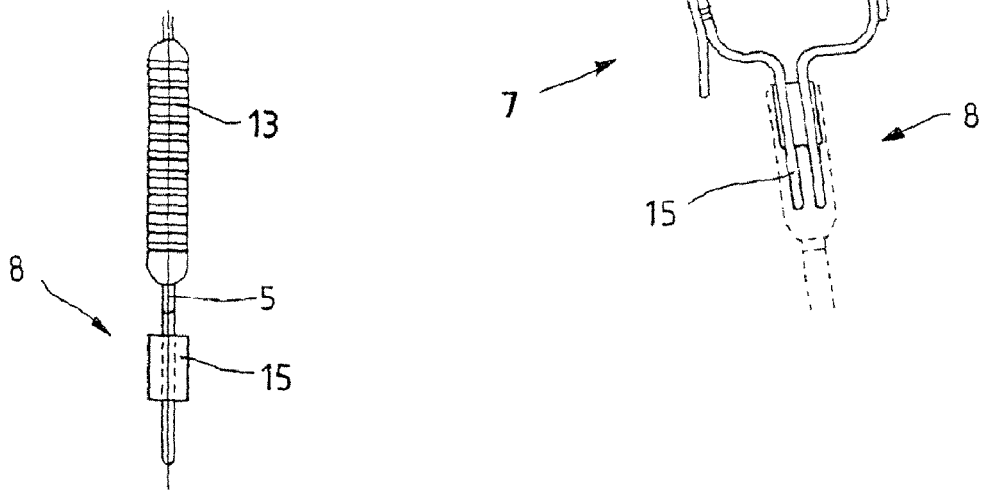
Figure 4C:
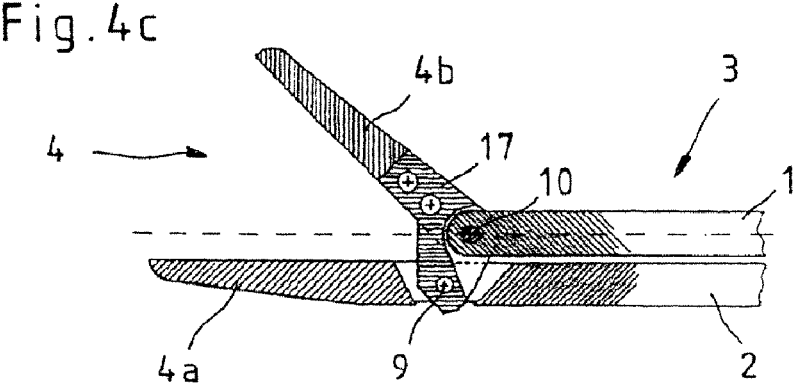
Figure 4D:
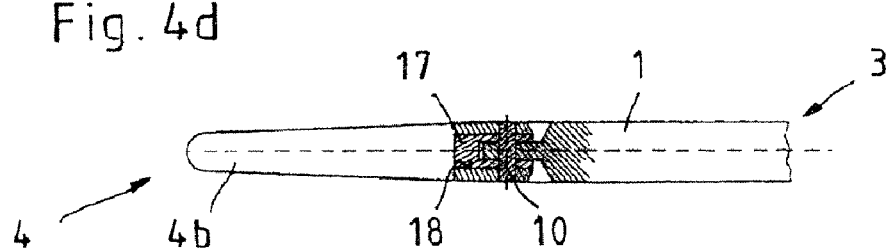
FIG. 4d shows an overhead view of the depiction shown in FIG. 4c.
Figure 5:
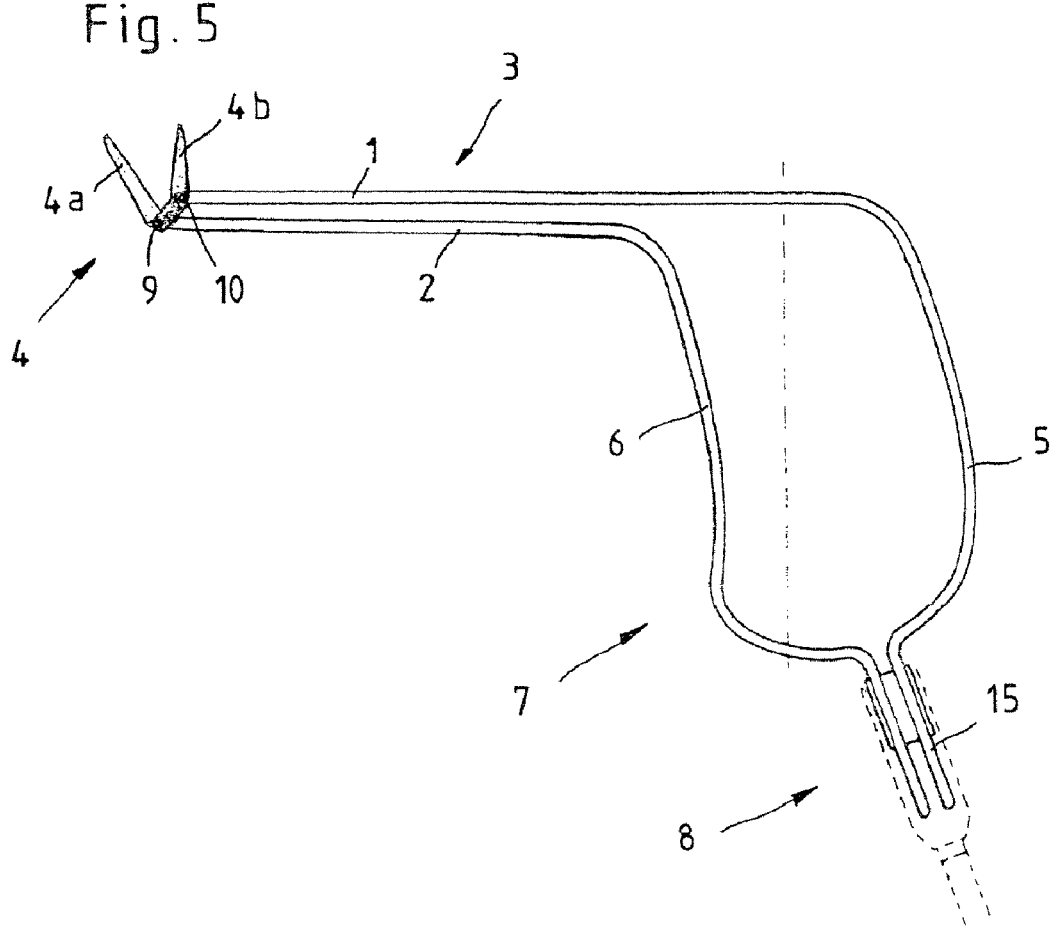
FIG. 5 shows a side view of a fifth embodiment of a medical cutting and/or holding instrument according to the invention.
Figure 6A:
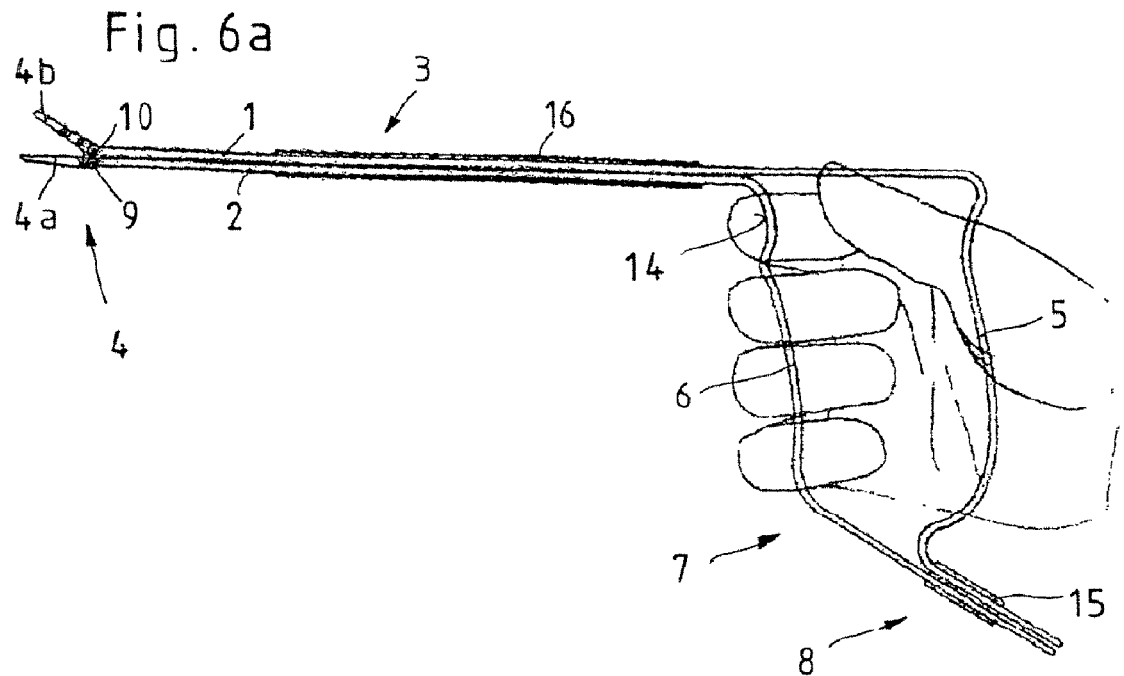
FIG. 6a shows a side view of a sixth embodiment of a medical cutting and/or holding instrument according to the invention.
Figure 6B:
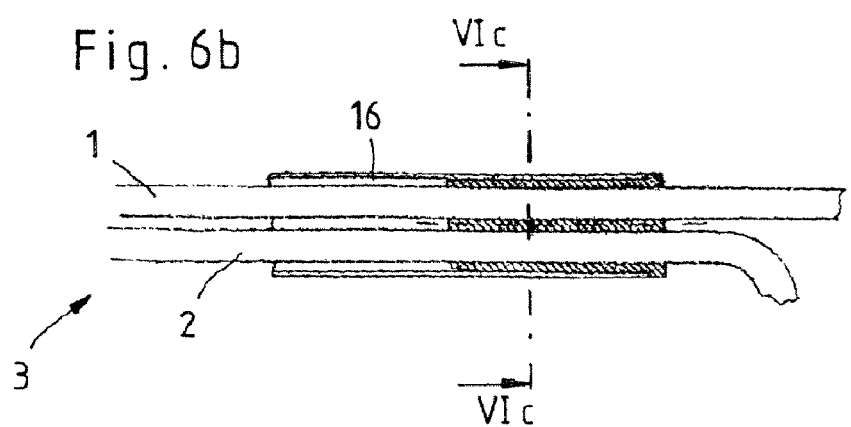
Figure 6C:
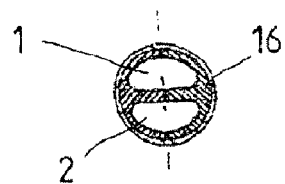
FIG. 6c shows a section along the line VIC-VIC shown in FIG. 6b.

The illustrated instruments, moreover, can be divided into two groups with differently configured handles 7, namely, first, the instruments shown in FIGS. 1, 2, and 3, in which the gripping members 5 and 6 of the handle 7, which are connected without joints with one another, form a single unit component and, second, the instruments shown in FIGS. 4a, 5, and 6a, in which the gripping members 5 and 6 of the handle 7 are connected without joints to one another by a coupling element 8.

In all cases the illustrated medical cutting and/or holding instruments are distinguished in that they consist of only a few components and in the area of the handle 7 dispense completely with any complex joint mechanism.

To open and close the jaw members 4a and 4b of the tool 4 by the handle 7 in the illustrated instruments, the gripping members 5 and 6, either of the handle 7 produced as a single unit according to FIGS. 1 to 3, or else the gripping members 5 and 6 of the handle 7 connected with one another by the coupling element 8, according to FIGS. 4a to 6a, are configured so that they can be displaced with respect to one another by spring elasticity. The gripping members 5 and 6, preferably produced from round or flat precious metal and connected as a single unit with the respective shaft rods 1 and 2 of the shaft 3, are configured here in such a way that, upon clasping the handle 7 the gripping member 5 remains essentially rigid and the gripping member 6 can be drawn forward by pulling the finger against the rigid gripping member 6. As a result of the spring elasticity of the material of the gripping members 5 and 6 that are connected with one another, the gripping member 6 immediately springs back into the illustrated starting position again.

Because of the single unit configuration of the gripping members 5 and 6 of the handle 7, each with one shaft rod 1 and 2 of the shaft 3, there results an essentially rigid shaft rod 1, which is configured as a single unit with the rigid gripping member 5, as well as an essentially axially movable shaft rod 2, which is configured as a single unit with the flexibly movably gripping member 6.

As can further be seen from the side views of the various instruments, the jaw member 4a of the tool 4 is configured rigidly as a single unit with the shaft rod 2, which in turn is configured as a single unit with the flexibly movable gripping member 6. The structure of the tool 4 with a rigid jaw member 4a and a rotatable jaw member 4b can be seen in particular in FIG. 4c.

The jaw member 4b configured as a rotatable tipping gear can rotate around coupling points 9 and 10 and is mounted on the rigid shaft rod 1 and the rigid jaw member 4a, so that the coupling points 9 and 10 take the form of mounting bolts. The rotatable mounting here is configured in such a way that the rotatable jaw member 4b is connected with the axially movable shaft rod 2 by the coupling point 9 and displacement of this shaft rod 2 causes rotation of the rotatable jaw member 4b around the coupling point 10 on the rigid shaft rod 1.

By modifying the distance of the two coupling points 9 and 10 of the rotatable jaw member 4b, it is possible to realize various translation ratios in order to be able to exert more or less force by the jaw members 4a and 4b of the tool 4, depending on the area of application of the instrument.

Because the gripping members 5 and 6, because of the spring elasticity, always more or less automatically assume the illustrated starting point in which the tool 4 is found in the open position, it can be advantageous, in particular in the configuration of the tool as a holding instrument, to provide a stopping mechanism 11, as seen in FIG. 3, by which the gripping members 5, 6 of the handle 7 and/or the shaft rods 1, 2, at least in a closed position of the tool 4, can be fixed in their respective position with respect to one another. In the embodiment shown in FIG. 3, the stopping mechanism 11 is configured as a latch 11a on the movable gripping member 6, which, pre-tensioned as a stopping mechanism by a spring element 11b, engages in a notched toothing 11c configured in the rigid shaft rod 1. The stopping mechanism is released in the illustrated embodiment by means of an index finger support 12 configured as a toggle switch.

To facilitate gripping of the handle 7 for the operator and to ensure a secure, precise operation of the medical cutting and/or holding instrument, in keeping with the embodiment shown in FIG. 2 the handle 7 is configured as flattened in the area of the gripping members 5 and 6.

FIGS. 4a and 6a show alternative embodiments for improving the maneuverability, according to which, as per FIG. 4a, a gripping plate 13 is secured on gripping members 5 and 6 of the handle 7 and, as per FIG. 6a, at least one finger groove 14 is configured on at least one gripping member 6 of the handle 7. In addition to the previously described connection of the gripping members 5 and of the handle 7 by the coupling element 8, the medical instruments shown in FIGS. 4a to 6a are distinguished from the instruments shown in FIGS. 1 to 3 in that, in addition to the use as mere cutting and/or holding instruments, they are configured in such a way that they can be used as monopolar or bipolar instruments for electro-surgery.

In so-called electro-surgery, high-frequency energy is directed to the surgical area by the medical instrument and is transformed in the tissue into heat energy, so that at the transformation area, temperatures of about 60 to 100 degrees Celsius occur. This electro-surgery is used for coagulating tissue and small vessels and for cutting or severing tissue.

To use the illustrated medical instruments in electro-surgery, the gripping members 5 and 6 of the handle 7 are connected with a connecting plug 15, by which the high-voltage current is introduced into the instrument and, in bipolar application, is also diverted out again. In the embodiments shown in FIGS. 4a to 61, the connecting plug 15 is configured as a coupling element 8 that connected the two gripping members 5, 6 of the handle 7 to one another.

In monopolar application, the desired thermal effect occurs only at the so-called active electrode, the distal end of the medical instrument. This effect is achieved when the active electrode has a clearly smaller contact surface than the so-called neutral electrode, on which the patient lies. The current flow in monopolar high-frequency (HF) application proceeds from a HF current source through the connecting plug 15 into the medical instrument and continues further by way of the gripping members 5 and 6 as well as the shaft rods 1 and 2 to the jaw members 4a and 4b of the tool 4. Upon contact by the tool 4 with the patient tissue, the current circuit closes and the entire high-frequency current required for the heat effect flows through the tissue volume to the neutral electrode. Because of the small contact surface of the tool that acts as an active electrode, a high HF current density develops only in proximity to the tool and only in this same area does a heat development occur with correspondingly high temperature.

In bipolar application, the HF current flows only in a tissue volume between two electrodes of equal type and equal size, namely the jaw members 4a and 4b of the tool 4. The distance between the two electrodes is very small, and the HF current flows only through a relatively small tissue volume. The heat development occurs exclusively between the two electrodes, the jaw members 4a and 4b. The current flow, in the bipolar HF application, proceeds from a HF current source by way of the connecting plug 15 into the medical instrument and continues by way of the rigid gripping member 5 and the rigid shaft rod 1 to the rotatable jaw member 4b of the tool 4. As soon as both jaw members 4a and 4b are in contact with the patient's tissue, the current circuit closes and the HF current flows through the rigid jaw member 4a of the tool 4 further through the axially slidable shaft rod 2 and the movable gripping member 6 of the handle 7 back through the connecting plug 15 to the HF current source.

To protect the operator and to protect tissue parts that are not to be handle, all current-bearing parts, including the two jaw members 4a and 4b of the tool 4, are configured as electrically insulated. In the embodiment illustrated in FIGS. 6a to 6c the insulation is configured as a contracting hose, which completely surrounds the parts that are to be insulated, as can be seen in particular in the section views of FIGS. 6b and 6c. The illustrations show only schematic depictions of the insulation of the shaft rods 1 and 2 of the shaft 3, although in practice the gripping members 5 and 6 of the handle 7 are also configured as insulated.

As can be seen from the illustrations, the shaft rods 1 and 2, which run separately from one another with the gripping members 5 and 6 of the handle 7 shaped to match them, without joints, in single unit construction, offer clearly favorable insulating conditions for use in applying and removing electric high-voltage current.

To prevent premature conducting of current into the current-removing shaft rod 2, in the embodiment shown in FIGS. 4a to 4d the rotatable jaw member 4b is mounted on the rigid jaw member 4a and on the rigid shaft rod 1 by means of an electrically insulated jointed strip 17 that is electrically insulated or that consists of an electrically non-conductive material. As can be seen in particular from the detailed views of FIGS. 4c and 4d, the jointed strip 17 is positioned in a longitudinal slit 18 of the rotatable jaw member 4b, so that the high-voltage current is preferably conducted from the rigid shaft rod 1 through the mounting bolts of the coupling points 10 into the rotatable jaw member 4b.

The medical cutting and/or holding instruments that are configured as seen in the illustrations, in addition to their multilateral uses, are distinguished in that they are simply constructed to consist of only a few components. In addition to the result that such instruments can be constructed and installed simply and quickly, and thus at reasonable cost, they are all characterized by being easy to clean.

What is claimed is:

1. A medical cutting and/or holding instrument having a shaft, a tool mounted on the distal end of the shaft and consisting of two jaw members, and a handle, positioned on the proximal end of the shaft and consisting of two gripping members, which serves to open and close the jaw members of the tool, the shaft consisting of two shaft rods that are each configured without joints and in one piece with one of the gripping members of the handle, characterized in that the tool is composed of a rigid jaw member and a pivotable jaw member, wherein the pivotable jaw member is connected with its respective shaft rod by a first coupling point and displacement of this shaft rod causes pivoting of the pivotable jaw member about a second coupling point on the other shaft rod and that the gripping members of the handle can be moved relative to each other by spring elasticity.

2. A medical cutting and/or holding instrument according to claim 1, characterized in that the gripping members of the handle are connected to one another by a coupling element.

3. A medical cutting and/or holding instrument according to claim 1, characterized in that the handle with two gripping members is configured as a single-unit component.

4. A medical cutting and/or holding instrument according to claim 1, characterized in that the handle is of flattened configuration, at least in the area of one gripping member.

5. A medical cutting and/or holding instrument according to claim 1, characterized in that on at least one gripping member of the handle at least one finger groove is configured.

6. A medical cutting and/or holding instrument according to claim 1, characterized in that a gripping plate can be secured on at least one gripping member of the handle.

7. A medical cutting and/or holding instrument according to claim 1, characterized in that one jaw member of the tool is configured rigidly as a single unit with one shaft rod and the other jaw member is mounted so that it can pivot about coupling points on the other shaft rod and on the rigid jaw member.

8. A medical cutting and/or holding instrument according to claim 7, characterized in that the distance between the coupling points of the pivotable jaw member can be modified.

9. A medical cutting and/or holding instrument according to claim 1, characterized in that the gripping members of the handle and/or the shaft rods, at least when the tool is in a closed position, can be fixed in their particular position with respect to one another by a stopping mechanism.

10. A medical cutting and/or holding instrument according to claim 1 for use as a monopolar or bipolar instrument in electro-surgery, characterized in that the gripping members of the handle are connected with a connecting plug.

11. A medical cutting and/or holding instrument according to claim 10, characterized in that the connecting plug is configured as a coupling element connecting the two gripping members of the handle with one another.

12. A medical cutting and/or holding instrument according to claim 10, wherein said instrument includes at least one current-conducting part and wherein said at least one current conducting part is electrically insulated, in particular by means of a shrinkable sleeve.

13. A medical cutting and/or holding instrument according to claim 10, characterized in that the pivotable jaw member is mounted by means of an electrically insulated jointed strip on the rigid jaw member and on the shaft rod.

* * * * *